(12) United States Patent
Kane

(10) Patent No.: US 9,945,883 B2
(45) Date of Patent: Apr. 17, 2018

(54) PIPETTE SYSTEM

(71) Applicant: LIFE TECHNOLOGIES CORPORATION, Carlsbad, CA (US)

(72) Inventor: Nathan Kane, Guilford, CT (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 439 days.

(21) Appl. No.: 14/680,831

(22) Filed: Apr. 7, 2015

(65) Prior Publication Data

US 2015/0285831 A1    Oct. 8, 2015

Related U.S. Application Data

(60) Provisional application No. 61/976,864, filed on Apr. 8, 2014.

(51) Int. Cl.
*G01N 35/10* (2006.01)

(52) U.S. Cl.
CPC ..... *G01N 35/1081* (2013.01); *G01N 35/1011* (2013.01); *G01N 2035/103* (2013.01)

(58) Field of Classification Search
CPC ........... G01N 35/1081; G01N 35/1011; G01N 2035/103

USPC .............................. 73/864.11, 864.24, 864.25
See application file for complete search history.

(56) References Cited

U.S. PATENT DOCUMENTS

| | | | |
|---|---|---|---|
| 4,977,786 A | 12/1990 | David | |
| 5,012,683 A | 5/1991 | Davis | |
| 5,612,227 A * | 3/1997 | Inoue | G01F 23/165 422/547 |
| 7,479,391 B2 | 1/2009 | Bjornson et al. | |
| 8,216,527 B2 | 7/2012 | Dzuong | |
| 8,287,820 B2 | 10/2012 | Williams et al. | |
| 8,808,625 B2 * | 8/2014 | Aoki | B01L 3/0241 422/501 |
| 2005/0194394 A1 * | 9/2005 | Ueda | G01N 35/1011 221/4 |
| 2012/0156098 A1 * | 6/2012 | Sano | G01N 35/10 422/68.1 |
| 2012/0321520 A1 * | 12/2012 | Okanojo | G01N 21/6428 422/82.08 |

* cited by examiner

*Primary Examiner* — Peter Macchiarolo
*Assistant Examiner* — Anthony W Megna Fuentes

(57) ABSTRACT

A pipetting system includes a rail; a carriage to engage the rail, the carriage movable relative to the rail substantially along a first axis; a pipette pump slidably engaged with the carriage, the pipette pump slidable relative to the carriage substantially along the first axis; and a sensor to detect movement of the pipette pump relative to the carriage.

14 Claims, 3 Drawing Sheets

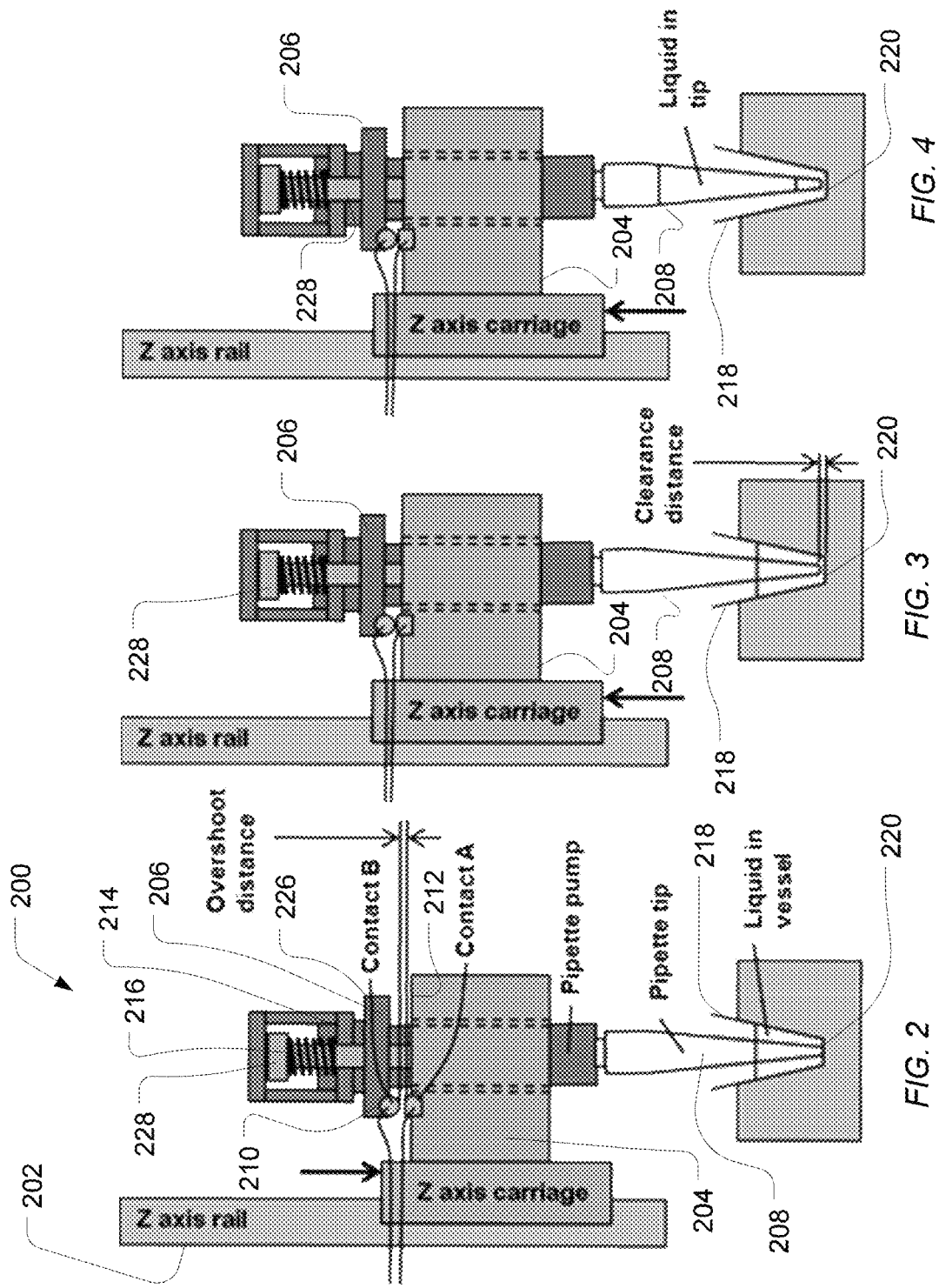

PIPETTE SYSTEM

CROSS-REFERENCE TO RELATED APPLICATION(S)

This application claims benefit of U.S. Provisional Application No. 61/976,864, filed Apr. 8, 2014 and entitled "PIPETTING SYSTEM," which is incorporated herein by reference in its entirety.

FIELD OF THE DISCLOSURE

This disclosure, in general, relates to pipette systems and methods for using same.

BACKGROUND

In advancing scientific fields, ever smaller volumes are used in testing and experimentation. In the genetic sciences, small aliquots of expensive reagents are used in genetic sequencing. In particular, nucleotide reagents, enzymes and oligonucleotide primers are expensive. Residual liquid left in vessels after aspiration represents significant cost.

SUMMARY

A pipette system includes a rail, a carriage engaging the rail, a pipette pump slidably engaged with the carriage. A sensor can detect relative movement of the carriage and pipette pump. A method of aspirating liquid from a vessel includes detecting contact of a pipette tip and a vessel bottom surface using the sensor and moving the carriage a distance to provide a clearance distance between the pipette tip and the bottom surface of a vessel.

BRIEF DESCRIPTION OF THE DRAWINGS

The present disclosure may be better understood, and its numerous features and advantages made apparent to those skilled in the art by referencing the accompanying drawings.

FIG. 2, FIG. 3, FIG. 4, FIG. 5, and FIG. 6 include illustrations of an exemplary pipette system and methods for its use.

The use of the same reference symbols in different drawings indicates similar or identical items.

DETAILED DESCRIPTION

In an exemplary embodiment, a pipette system includes a carriage attached to a rail. The rail can form part of a one, two or three-dimensional robotic system for moving the carriage along one or more axes. A pipette pump can be slidably engaged with the carriage. For example, when a pipette tip attached to the pipette pump contacts a surface, the pipette pump can slide relative to the carriage in a direction opposite the movement of the carriage. The pipette system can include a sensor to detect when the pipette pump moves relative to the carriage, or in particular, when the pipette pump moves from a rest position in which the pipette pump is engaged with a stop structure, for example, formed by the carriage. When movement of the pipette pump is detected, the carriage can reverse direction and move a set distance in the reverse direction, move until the pipette pump returns to the rest position, or a combination thereof. As such, the pipette tip can be positioned proximal to the bottom surface of a vessel without contacting the bottom surface of the vessel.

In a further exemplary embodiment, the pipette system can include a second stop structure to engage the pipette pump when it moves a distance from the rest position. A force member can engage the second stop structure to provide a force opposite to the pipette pump. In an example, when the pipette pump distal end is inserted into a tip, the pipette pump can contact the second stop structure which provides a desirable force to engage the pipette tip. The force member thus provides desirable force or a range of force to engage the pipette tip.

Figure 1:
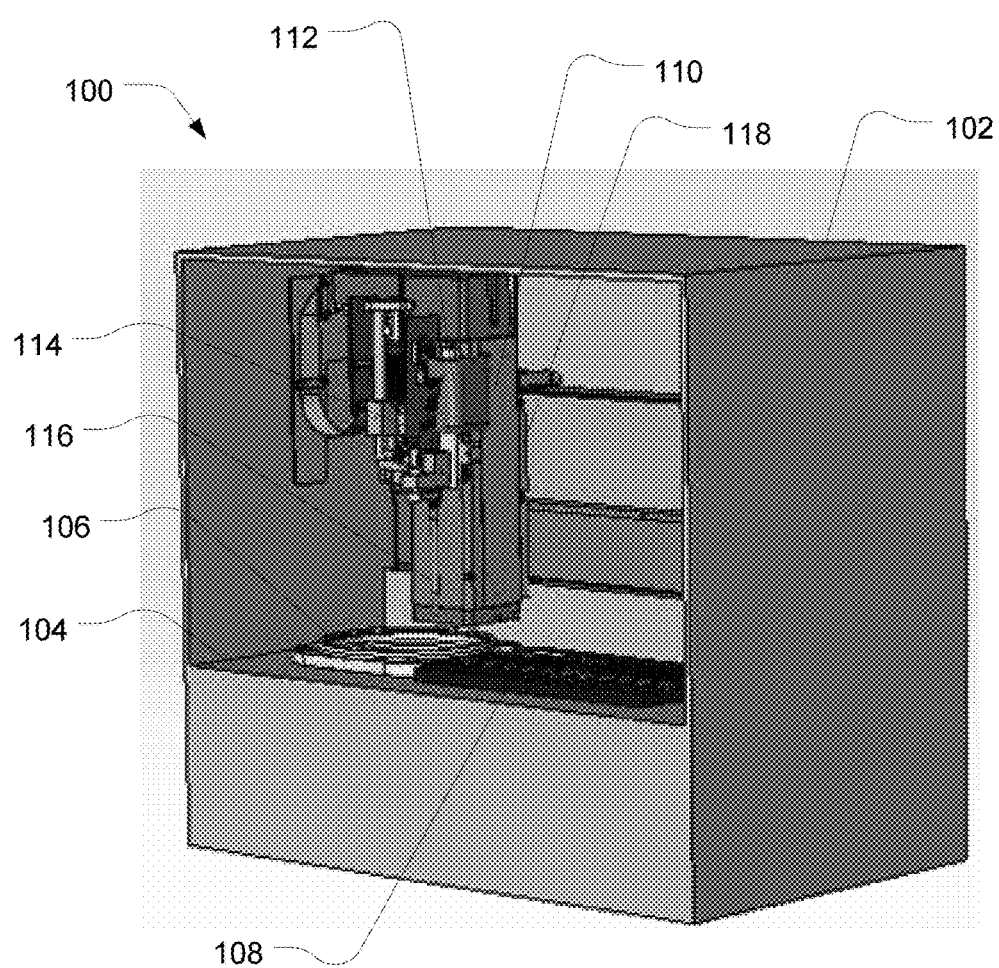
FIG. 1 includes an illustration of an exemplary automated sample preparation station.

FIG. 1 illustrates an exemplary sample preparation system 100. Within an enclosure 102, a platform 104 supports one or more stations 108 to hold vessels and pipette tips and can support a centrifuge 106. A robotic system 118 can move in at least one direction, such as two dimensions, or three dimensions. A carriage 112 is attached to a rail 110 of the robotic system 118. A pipette pump 114 is slidably engaged with the carriage 112, and a distal end of the pipette pump 114 can engage a pipette tip 116. The robotic system 118 can operate to move the pipette pump 114 and pipette tip 116 into position in and out of vessels or to positions associated with the centrifuge 106 to perform sample preparation functions.

As illustrated in FIG. 2, a rail 202 of the robotic system 200 can engage a carriage 204. The carriage 204 can be motivated in a direction substantially long an axis of the rail 202. As illustrated, the carriage 204 can be motivated up and down along a z-axis rail 202. A pipette pump 206 can be slidably connected with the carriage 204. In a particular example, the pipette pump 206 can slide within the carriage substantially along the axis optionally bound by lower or upper stop structures. For example, the pipette pump 206 can slidably engage the carriage 204 using guide structures or bushings.

Optionally, a motivator (not illustrated) can apply a force on the pipette pump 206 relative to the carriage 204 when the pipette pump 206 moves between engaging a lower stop structure and upper stop structure. In an example, the motivator can apply a force to return the pipette pump 206 into contact with the lower stop structure 212, for example, formed by the carriage 204. An exemplary motivator includes a mechanical spring, an air cylinder, a solenoid, or any combination thereof. Alternatively, a weight of the pipette pump 206 can act to return the pipette pump 206 into contact with a stop structure 212 associated with the carriage 204. In a particular example, the carriage 204 includes a surface which defines a lower stop structure 212. Alternatively, a lower stop structure can be defined separately from the carriage. For example, the motivator can include a tension spring coupled between a flange 226 of the pipette pump 206 and the stop structure or surface 212. In another example, the motivator can include a compression spring disposed between the flange 226 and a fixed upper structure, such as an upper stop structure or another upper surface fixed relative to the carriage 204. Alternatively, the motivator can be a compression spring disposed between the carriage 204 and an optional flange disposed on the pipette pump 206 below the carriage 204.

The pipette system 200 further includes a sensor 210, which can detect when the pipette pump 206 moves from a rest position in contact with a stop structure 212, for example, in contact with the carriage 204. In another example, the sensor 210 can detect a position of the pipette pump 206 relative to the carriage 204. An exemplary sensor can include an electrical contact, a Hall effect sensor, a capacitive sensor, an optical position sensor, a linear optical encoder, a linear variable differential transformer position sensor, or a combination thereof. In a particular example, the sensor 210 includes an electrical contact that disengages when the pipette pump 206 moves from a rest position, for example, moving to disengage from the lower stop structure.

The pipette system 200 can further include an upper stop structure 214. When the pipette pump 206 moves relative to the carriage 204, for example, away from a rest position or against the first stop surface 212, the pipette pump can move a distance until it contacts the upper or second stop structure 214. In an example, the second stop structure 214 can be a hard stop immovably secured to a position relative to the carriage 204. Alternatively, the second stop structure 214 can be movable and can engage a force member 216 providing an opposing force to that of the pipette pump 206 when the pipette pump 206 contacts the second stop structure 214. In such an example, the upper stop structure 214 can permit some movement of the pipette pump 206 when a force provided by the pipette pump 206 on the upper stop structure 214 exceeds an opposing force provided by the force member 216. In an example, the force member 216 can include a weight, a mechanical spring, an air cylinder, a solenoid, or a combination thereof. In a particular example, the second stop structure 214 is moveable relative to the carriage 204 along an axis or rod 228 secured to or part of the carriage. A force member 216, such as a spring, is secured to the upper stop structure 214 and a flange of the axis or rod 228. When the pump 206 moves against the upper stop structure 216, the force member 216 provides an opposing force, for example, in accordance with a spring constant, until the force member 216 is fully compressed, at which point, the upper stop structure 216 becomes a fixed stop relative to the carriage 204.

In an example, the pipette system 200 can be used to supply liquid to the vessel, retrieve liquid from a vessel, mix liquid within a vessel by aspirating and discharging, or any combination thereof. For example, when a pipette tip 208 is engaged with the pipette pump 204, a robotic system 200 can position the pipette tip over a vessel 218. The carriage 204 can move substantially along an axis of the rail 202, lowering the pipette tip 208 into the vessel 218. When a distal end of the pipette tip 208 contacts a lower surface 220 of the vessel 218, as illustrated in FIG. 2, the pipette pump 206 moves relative to the carriage 204 in a direction opposite the carriage's 204 movement along the rail 202. For example, as the carriage 204 moves substantially along an axis of the rail 202 in a downward direction, the pipette pump 206 may be stationary when the pipette tip 206 is in contact with the lower surface 220, causing a relative movement between the pipette pump 206 and the carriage 204 substantially along the axis of the rail 202 in a direction opposite the movement of the carriage 204.

The sensor 210 can detect the relative movement of the pipette pump 206 and the carriage 204. In particular, the pipette pump 206 disengages from a rest surface or lower stop structure 212. As such, a change is detected by the sensor 210. Optionally, the carriage 204 can move an additional overshoot distance following detection of the relative movement of the pipette pump 206 and the carriage 204. In an example, the overshoot distance can be in a range of 0.001 mm to 2 mm. In particular, the position of the carriage 204 when the sensor 210 detects relative movement of the pump 206 and the carriage 204 can be designated as the positioning of the bottom of the vessel 220. The carriage 204 can then reverse direction moving substantially along the axis of the rail 202 and bringing the pipette pump 206 back into contact with the lower stop 212. Optionally, the carriage can be moved an additional clearance distance once the sensor detects a return of the pipette pump 206 into contact with the lower stop structure 212, as illustrated in FIG. 3. Alternatively, the clearance distance can be applied from the initially detected position of the carriage designated as the lower surface position.

As illustrated in FIG. 3, the pipette tip 208 is positioned a clearance distance from the lower surface 220 of the vessel 218. As illustrated in FIG. 4, liquid can be aspirated into the pipette tip 208 using the pipette pump 206, limiting the amount of residual liquid remaining in the vessel 218. In particular, the amount of liquid remaining in the vessel 218 following aspiration can be less than 2 microliters. Optionally, the pipette pump can aspirate a volume equal to the nominal fluid volume of the vessel 218. In further example, the pipette pump 206 can aspirated a volume that includes both the nominal fluid volume of the vessel 218 and a specified additional volume.

Following aspiration of the liquid within the vessel 218, the carriage can be motivated in a direction illustrated as an upward direction substantially along the axis of the rail 202, moving the pipette tip 208 out of the vessel 218. The aspirated liquid within the pipette tip 208 can be deposited in another vessel or can be discarded in accordance with a sample preparation procedure.

Figures 5, 6:
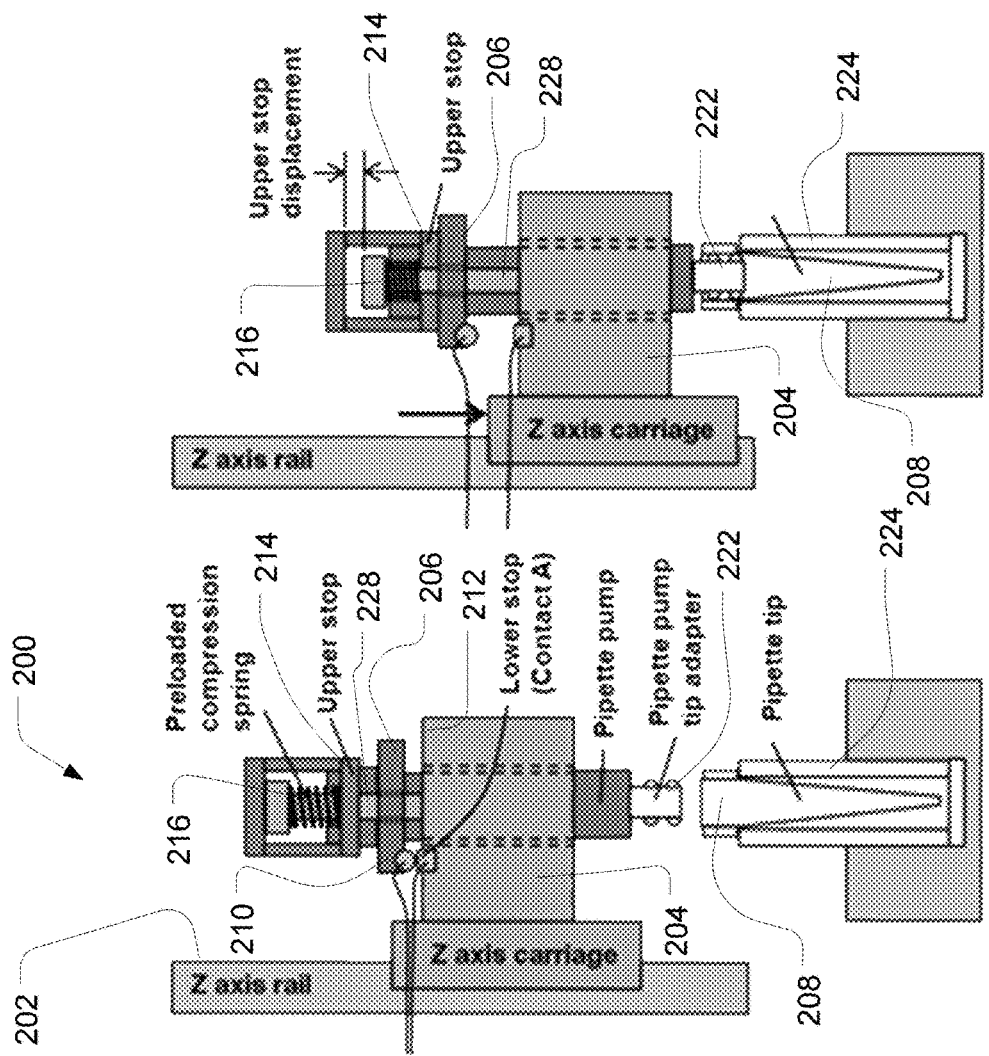

As illustrated in FIG. 5, the pipette system 200 can be used to engage the pipette tip 208 within a tip holder 224 using a selected force or a range of forces. In particular, the pipette pump 206 includes a tip adapter 222 at a distal end of the pump 206. Once positioned over the pipette tip 208, the carriage 204 can move substantially along an axis of the rail 202 to engage the pipette tip adapter 222 with the pipette tip 208. Upon initially engaging with the pipette tip 208, the pipette pump 206 moves relative to the carriage 204. In particular, the carriage 204 can continue moving in the illustrated downward direction while the pipette pump 206 is stationary and thus moves relative to the carriage 204 in a direction opposite carriage's movement relative to the rail 202. The sensor 210 can detect the relative movement of the pipette pump 206 and the carriage 204.

As illustrated in FIG. 6, the carriage 204 can continue moving in a direction towards the pipette tip 208. The pipette pump 206 engages an upper stop structure 214. The upper stop structure 214 applies a force to the pipette pump 206 in a direction opposite the force being applied by the pipette pump 206 on the upper stop structure 214 and in a direction substantially parallel to the movement of the carriage 204. Optionally, a force member 216 can apply the force or a range of forces depending on the movement of the carriage 204 on the upper stop structure 214 and opposite the force applied by the pump 206. In particular, the force applied to the tip adaptor 222 or the tip 208 can be related to the upper stop displacement; e.g., approximately in accord with a spring constant. For example, the force member 216, such as a spring, can apply a force to a moveable upper stop structure 214 based on compression distance toward a fixed flange associated with a rod 228 secured to the carriage 204.

Upon detecting relative movement of the pipette pump 206 and the carriage 204, the carriage 204 can be moved a set distance substantially along an axis of the rail 202, which results in the pipette pump 206 engaging the upper stop structure 214 and displacing the upper stop structure 214 to an extent that applies a set force on the pipette tip adapter 222 as it is applied to the pipette tip 208 within the pipette tip holder 224. Alternatively, the sensor 210 can detect the distance that the pipette pump 206 moves relative to the carriage 204. In further example, an additional sensor can be engaged with the upper stop structure 214 to determine when a desired stop displacement has occurred. For example, the additional sensor can include an electrical contact, a Hall effect sensor, a capacitive sensor, an optical position sensor, a linear optical encoder, a linear variable differential transformer position sensor, or a combination thereof Following engaging the pipette tip 208 with the pipette tip adapter 222, the carriage 204 can move in an opposite direction substantially along an axis of the rail 202 to remove the pipette tip 208 from the tip holder 224. The pipette tip 208 and the pipette system 200 can be used to transfer liquids and can perform other functions related to sample preparation.

In a further example, a robotic system of the sample preparation device can be automatically calibrated or can automatically test for tip engaging errors. For example, the robotic system can move the pipette system into position over a hole or slot within the deck. The pipette system can then detect when, during a down movement of the carriage, the pipette tip adapter enters the hole or slot or touches a horizontal reference surface. In such a manner, the system can perform self-calibration and check z-direction calibration.

In particular, embodiments of the pipette system provide particular technical advantages. For example, the pipette system can reliably aspirate liquid vessel, leaving less than 2 µL in the vessel. Such reliable aspiration of liquid from a vessel reduces costly reagent loss. In particular, the system can be used in recovering amplified beads or liquid dispersions of substrates with little loss. In a further example, the pipette system allows for low-cost z-axis application of the pipette tip to the pipette pump tip adapter with a repeatable and known force, limiting errors associated with tips dropping from the tip adapter or being stuck on the tip adapter following use.

In a first aspect, a pipetting system includes a rail; a carriage to engage the rail, the carriage movable relative to the rail substantially along a first axis; a pipette pump slidably engaged with the carriage, the pipette pump slidable relative to the carriage substantially along the first axis; and a sensor to detect movement of the pipette pump relative to the carriage.

In an example of the first aspect, the pipette pump is in a first position at rest, the sensor to detect whether the pipette pump is in the first position.

In another example of the first aspect and the above examples, the sensor is an electrical contact sensor, a Hall Effect sensor, a capacitive sensor, an optical position sensor, a linear optical encoder, a linear variable differential transformer position sensor, or a combination thereof.

In a further example of the first aspect and the above examples, the pipette system further includes a motivator coupling the pipette pump to the carriage to motivate the pipette pump in a first direction substantially along the first axis.

In an additional example of the first aspect and the above examples, the pipette system further includes a first stop structure, the pipette pump in contact with the first stop structure when in a first position. For example, the carriage defines the first stop structure. In another example, the first stop structure is to limit movement of the pipette pump in a first direction substantially along the first axis. In a particular example, the pipette system further includes a second stop structure to limit movement of the pipette pump in a second direction substantially along the first axis, the second direction opposite the first direction. For example, the first stop structure is at a lower position relative to the first axis than the second stop structure. In another example, the pipette system further includes a force member engaged with the second stop structure to provide force to the second stop structure opposite a force applied by the pipette pump. For example, the force member includes a spring, a weight, an air cylinder, a solenoid, or a combination thereof.

In a second aspect, a method of pipetting liquid from a vessel includes moving a carriage of a pipette system relative to a rail in a first direction substantially along a first axis. The pipette system includes the rail; the carriage to engage the rail, the carriage movable relative to the rail substantially along a first axis; a pipette pump slidably engaged with the carriage, the pipette pump slidable relative to the carriage substantially along the first axis; a sensor to detect movement of the pipette pump relative to the carriage. The method further includes detecting movement of the pipette pump relative to the carriage with the sensor, the movement indicative of a pipette tip secured to the pipette pump contacting a bottom surface of the vessel; moving the carriage of the pipette system in a second direction substantially along the first axis and opposite the first direction; and aspirating liquid within the vessel with the pipette pump.

In an example of the second aspect, moving the carriage in the second direction includes moving the carriage until the pipette pump is in a rest position. For example, the sensor detects whether the pipette pump is in the rest position.

In another example of the second aspect and the above examples, the method further includes moving the carriage an overshoot distance following detecting movement.

In a further example of the second aspect and the above examples, moving the carriage in the second direction includes moving the carriage a set distance in the second direction following detecting movement of the pipette pump.

In an additional example of the second aspect and the above examples, detecting movement of the pipette pump includes detecting that the pipette pump is not in a rest position.

In another example of the second aspect and the above examples, the carriage forms a stop structure, the pipette pump resting against the stop structure until the pipette tip contacts a surface.

In a further example of the second aspect and the above examples, aspirating includes aspirating a nominal volume associated with the vessel plus a set additional volume.

In a third aspect a method of applying a pipette tip includes moving a carriage of a pipette system relative to a rail in a first direction substantially along a first axis. The pipette system includes the rail; the carriage to engage the rail, the carriage movable relative to the rail substantially along a first axis; a pipette pump slidably engaged with the carriage, the pipette pump slidable relative to the carriage substantially along the first axis; a sensor to detect movement of the pipette pump relative to the carriage; a stop structure to limit movement of the pipette pump in a second direction substantially along the first axis, the second direction opposite the first direction; and a force member engaged with the stop structure to provide force to the stop structure opposite a force applied by the pipette pump. The method further includes engaging a pipette tip with the pipette pump, the pipette pump sliding in the second direction in response to engaging the pipette tip, the stop structure applying force to the pipette pump to secure the pipette tip.

As used herein, substantially along an axis refers to movement parallel to the axis ±15°, such as ±10°, or ±5°. While the pipette system is described as including a pipette pump slidably engaged with a carriage, a manifold fluidically connected to a pipette pump can be slidably engaged with the carriage in place of the pipette pump. References to axes within the system include a z-axis, which is substantially along a normal to a ground surface or parallel to gravity and is illustrated as up and down. Other orthogonal axes can be perpendicular to gravity.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A pipetting system comprising: a rail; a carriage to engage the rail, the carriage movable relative to the rail substantially along a first axis; a pipette pump slidably engaged with the carriage, the pipette pump slidable relative to the carriage substantially along the first axis; a sensor to detect movement of the pipette pump relative to the carriage; a first stop structure, the pipette pump in contact with the first stop structure when in a first position; wherein the first top structure is to limit movement of the pipette pump in a first direction substantially along the first axis; and a second stop structure to limit movement of the pipette pump in a second direction substantially along the first axis, the second direction opposite the first direction, wherein the first stop structure is at a lower position relative to the first axis than the second stop structure.

2. The pipette system of claim 1, wherein the pipette pump is in the first position at rest, the sensor to detect whether the pipette pump is in the first position.

3. The pipette system of claim 1, wherein the sensor is an electrical contact sensor, a hall effect sensor, a capacitive sensor, an optical position sensor, a linear optical encoder, or a linear variable differential transformer position sensor.

4. The pipette system of claim 1, wherein the carriage defines the first stop structure.

5. The pipette system of claim 1, further comprising a force member engaged with the second stop structure to provide force to the second stop structure opposite a force applied by the pipette pump.

6. The pipette system of claim 5, wherein the force member includes a spring, a weight, an air cylinder, or a solenoid.

7. A method of pipetting liquid from a vessel, the method comprising: moving a carriage of a pipette system relative to a rail in a first direction substantially along a first axis, the pipette system comprising: the rail; the carriage to engage the rail, the carriage movable relative to the rail substantially along the first axis; a pipette pump slidably engaged with the carriage, the pipette pump slidable relative to the carriage substantially along the first axis; a sensor to detect movement of the pipette pump relative to the carriage; detecting movement of the pipette pump relative to the carriage with the sensor, the movement indicative of a pipette tip secured to the pipette pump contacting a bottom surface of the vessel; moving the carriage of the pipette system in a second direction substantially along the first axis and opposite the first direction; and aspirating liquid within the vessel with the pipette pump, wherein moving the carriage in the second direction includes moving the carriage until the pipette pump is in a rest position.

8. The method of claim 7, wherein the sensor detects whether the pipette pump is in the rest position.

9. The method of claim 7, further comprising moving the carriage an overshoot distance following detecting movement.

10. The method of claim 7, wherein moving the carriage in the second direction includes moving the carriage a set distance in the second direction following detecting movement of the pipette pump.

11. The method of claim 7, wherein detecting movement of the pipette pump includes detecting that the pipette pump is not in a rest position.

12. The method of claim 7, wherein the carriage forms a stop structure, the pipette pump resting against the stop structure until the pipette tip contacts a surface.

13. The method of claim 7, wherein aspirating liquid includes aspirating a nominal volume associated with the vessel plus a set additional volume.

14. A method of applying a pipette tip, the method comprising: moving a carriage of a pipette system relative to a rail in a first direction substantially along a first axis, the pipette system comprising: the rail; the carriage to engage the rail, the carriage movable relative to the rail substantially along the first axis; a pipette pump slidably engaged with the carriage, the pipette pump slidable relative to the carriage substantially along the first axis; a sensor to detect movement of the pipette pump relative to the carriage; a first stop structure, the pipette pump in contact with the first stop structure when in a first position; a second stop structure to limit movement of the pipette pump in a second direction substantially along the first axis, the second direction opposite the first direction, wherein the first stop structure is at a lower position relative to the first axis than the second stop structure; and a force member engaged with the stop structure to provide force to the stop structure opposite a force applied by the pipette pump; and engaging a pipette tip with the pipette pump, the pipette pump sliding in the second direction in response to engaging the pipette tip, the stop structure applying force to the pipette pump to secure the pipette tip.

\* \* \* \* \*